(12) United States Patent
Rogers et al.

(10) Patent No.: US 12,319,660 B2
(45) Date of Patent: Jun. 3, 2025

(54) PREPARATION OF SUBSTITUTED DIAMINOPYRAZINE DICARBOXYLIC ACIDS

(71) Applicant: MediBeacon Inc., St. Louis, MO (US)

(72) Inventors: Thomas Rogers, St. Louis, MO (US); David Adams, St. Louis, MO (US); Xiaogang Hua, St. Louis, MO (US)

(73) Assignee: MediBeacon Inc., St. Louis, MO (US)

( * ) Notice: Subject to any disclaimer, the term of this patent is extended or adjusted under 35 U.S.C. 154(b) by 467 days.

(21) Appl. No.: 17/697,275

(22) Filed: Mar. 17, 2022

(65) Prior Publication Data

US 2022/0324818 A1  Oct. 13, 2022

Related U.S. Application Data

(60) Provisional application No. 63/168,512, filed on Mar. 31, 2021.

(51) Int. Cl.
*C07D 241/10* (2006.01)
*A61K 31/4965* (2006.01)
*C07D 241/26* (2006.01)

(52) U.S. Cl.
CPC .................................. *C07D 241/26* (2013.01)

(58) Field of Classification Search
CPC ........................... C07D 241/10; A61K 31/4965

USPC ...................................... 544/407; 514/255.06
See application file for complete search history.

(56) References Cited

U.S. PATENT DOCUMENTS

| | | |
|---|---|---|
| 2013/0136698 A1 | 5/2013 | Neumann et al. |
| 2019/0125901 A1 | 5/2019 | Debreczeny et al. |
| 2019/0154697 A1 | 5/2019 | Shieh |

OTHER PUBLICATIONS

Rajagopalan, R. et al., "Hydrophilic Pyrazine Dyes as Exogenous Fluorescent Tracer Agents for Real-Time Point-of-Care Measurement of Glomerular Filtration Rate" Journal of Medicinal Chemistry, 2011, 54:5048-5058.
International Search Report and Written Opinion for PCT/US2022/020754 dated Jun. 14, 2022, 9 pages.
International Search Report and Written Opinion for PCT/US/2022/020789 dated Jun. 14, 2022, 8 pages.
Subiros-Funosas, et al. "Oxyma: An Efficient Additive for Peptide Synthesis to Replace the Benzotriazole-Based HOBt and HOAt with a Lower Risk of Explosion", Chem. Eur. J., 2009, 15:9394-9403.
PubChem-CID-71077, "D-serine", created Sep. 16, 2004, retrieved at https://pubchem.ncbi.nlm.nih.gov/compound/71077.
PubChem-CID-9085, "L-Homoarginine", created Jun. 24, 2005, retrieved at https://pubchem.ncbi.nlm.nih.gov/compound/9085.
Extended European Search Report issued Mar. 10, 2025 in related EP Application No. 22781870.5, 7 pgs.

*Primary Examiner* — Bruck Kifle
(74) *Attorney, Agent, or Firm* — POLSINELLI PC (57) ABSTRACT

The present invention provides improved methods for preparing a compound comprising Formula (I).

26 Claims, 3 Drawing Sheets

PREPARATION OF SUBSTITUTED DIAMINOPYRAZINE DICARBOXYLIC ACIDS

CROSS-REFERENCE TO RELATED APPLICATIONS

This application claims priority to U.S. Provisional Application No. 63/168,512, filed Mar. 31, 2021, the contents of which are incorporated herein by reference in their entirety.

FIELD OF THE INVENTION

The present disclosure generally relates to an improved method for preparing the compound comprising Formula (I).

Figure 1:
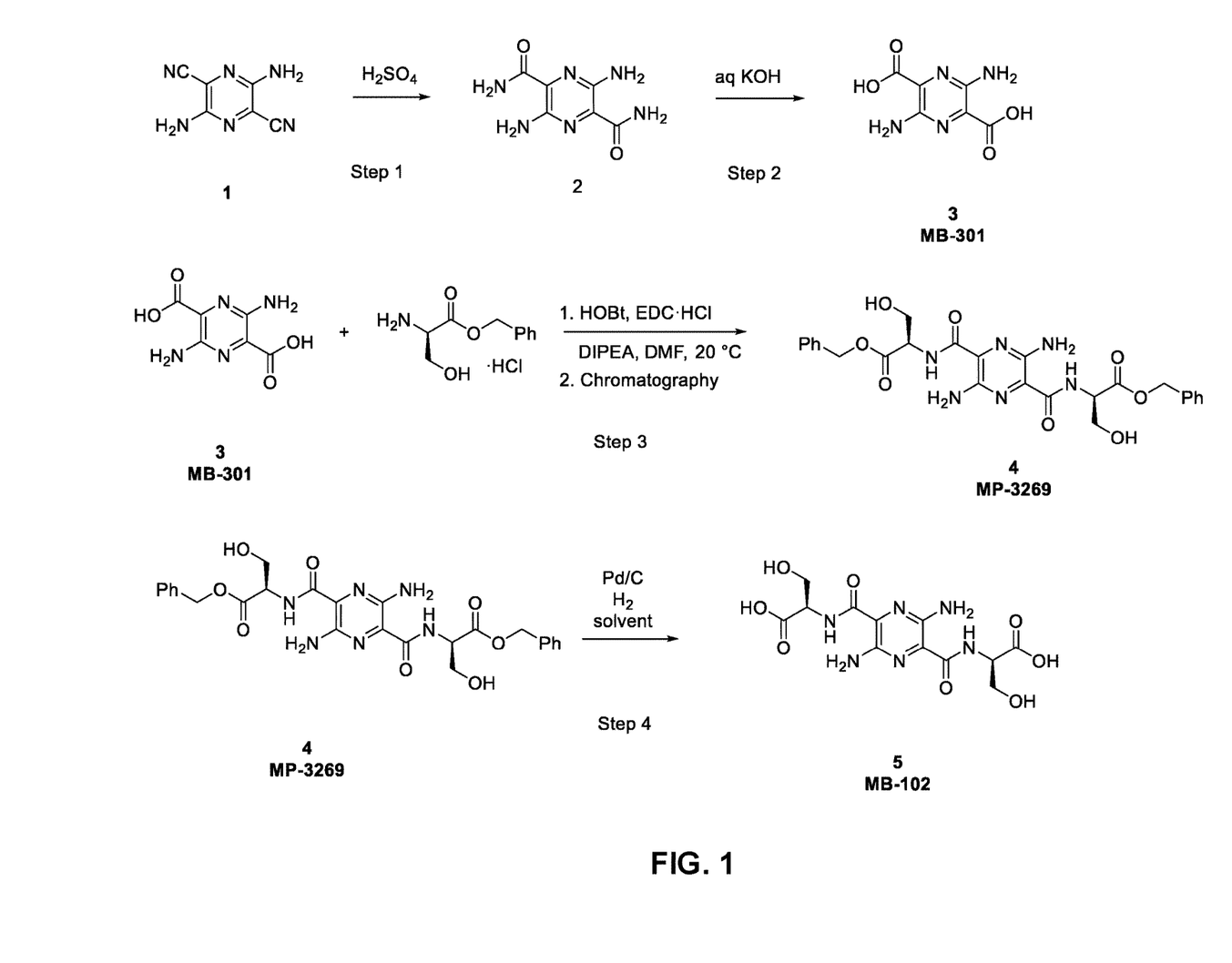
FIG. 1 illustrates the reaction scheme to prepare N,N'-[(3,6-diamino-2,5-pyrazinediyl)dicarbonyl]bis[D-serine] as depicted in prior art methods.

BACKGROUND OF THE INVENTION 3,6-Diamino-2,5-bis{N-[(1R)-1-carboxy-2-hydroxyethyl]-carbamoyl}pyrazine] (referred to MB-102) is a non-radioactive, exogenous agents useful for the monitoring of organ function in a human subject. The preparation of N,N'-[(3,6-diamino-2,5-pyrazinediyl)dicarbonyl]bis[D-serine] is prepared through a four step method as disclosed in previous applications as shown in FIG. 1. Step 1 of this four-step process hydrolyzes the aromatic nitrile groups of compound 1 using concentrated sulfuric acid forming the dicarboxamide compound 2. Step 2 hydrolyzes the dicarboxamide groups on compound 2 yielding dicarboxylic acid compound 3 (referred to as MB-301). Step 3 entails the coupling of compound 3 using HOBt (hydroxybenzotriazole), EDC HCl, diisopropylethylamine in N,N-dimethylformamide with the benzyl ester of (R) serine HCl yielding the product, compound 4 (referred to MP-3269). In order to remove impurities and provide a high purity of compound 4, the crude compound 4 is generally purified by chromatography. The purified compound 4 undergoes reductive debenzylation to form N,N'-[(3,6-diamino-2,5-pyrazinediyl)dicarbonyl]bis[D-serine] compound 5 in Step 4.

The main problem in further developing this process to a GMP (Good Manufacturing Practice) process is step 3 of the process. Step 3 utilizes chromatography and requires large quantities of various solvents. These factors increase the overall cost of the compound 4 and increases the waste for the process.

What is needed is an improved step 3 of the process which does not utilize chromatography, allows the crude compound 4 to have less impurities, and allows the material to be readily recrystallized to form a purified 4.

SUMMARY OF THE INVENTION

In one aspect, the present disclosure relates to a method for preparing the compound of Formula (I):

Formula (I)

The method comprises contacting 3,6-diamino-2,5-pyrazinedicarboxylic acid, an ester of an amino acid (AA ester) or a salt thereof, a polar aprotic solvent, a tertiary amine, ethyl-2-cyano-2-(hydroxyimino)acetate, and 1-ethyl-3-(3-dimethylaminopropyl)carbodiimide (EDC) hydrochloride under suitable reaction conditions to form the compound of Formula (I); wherein the ester portion of the AA ester is an $C_1$-$C_{10}$ unsubstituted alkyl or a $C_1$-$C_{10}$ substituted alkyl.

Other features and iterations of the invention are described in more detail below.

DETAILED DESCRIPTION OF THE INVENTION

Before the present invention is disclosed and described, it is to be understood that this invention is not limited to the particular methods, compositions, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Concentrations, amounts, and other numerical data may be expressed or presented herein in a range format. It is to be understood that such a range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 2 to about 50" should be interpreted to include not only the explicitly recited values of 2 to 50, but also include all individual values and sub-ranges within the indicated range. Thus, included in this numerical range are individual values such as 2, 2.4, 3, 3.7, 4, 5.5, 10, 10.1, 14, 15, 15.98, 20, 20.13, 23, 25.06, 30, 35.1, 38.0, 40, 44, 44.6, 45, 48, and sub-ranges such as from 1-3, from 2-4, from 5-10, from 5-20, from 5-25, from 5-30, from 5-35, from 5-40, from 5-50, from 2-10, from 2-20, from 2-30, from 2-40, from 2-50, etc. This same principle applies to ranges reciting only one numerical value as a minimum or a maximum. Furthermore, such an interpretation should apply regardless of the breadth of the range or the characteristics being described.

Figure 2:
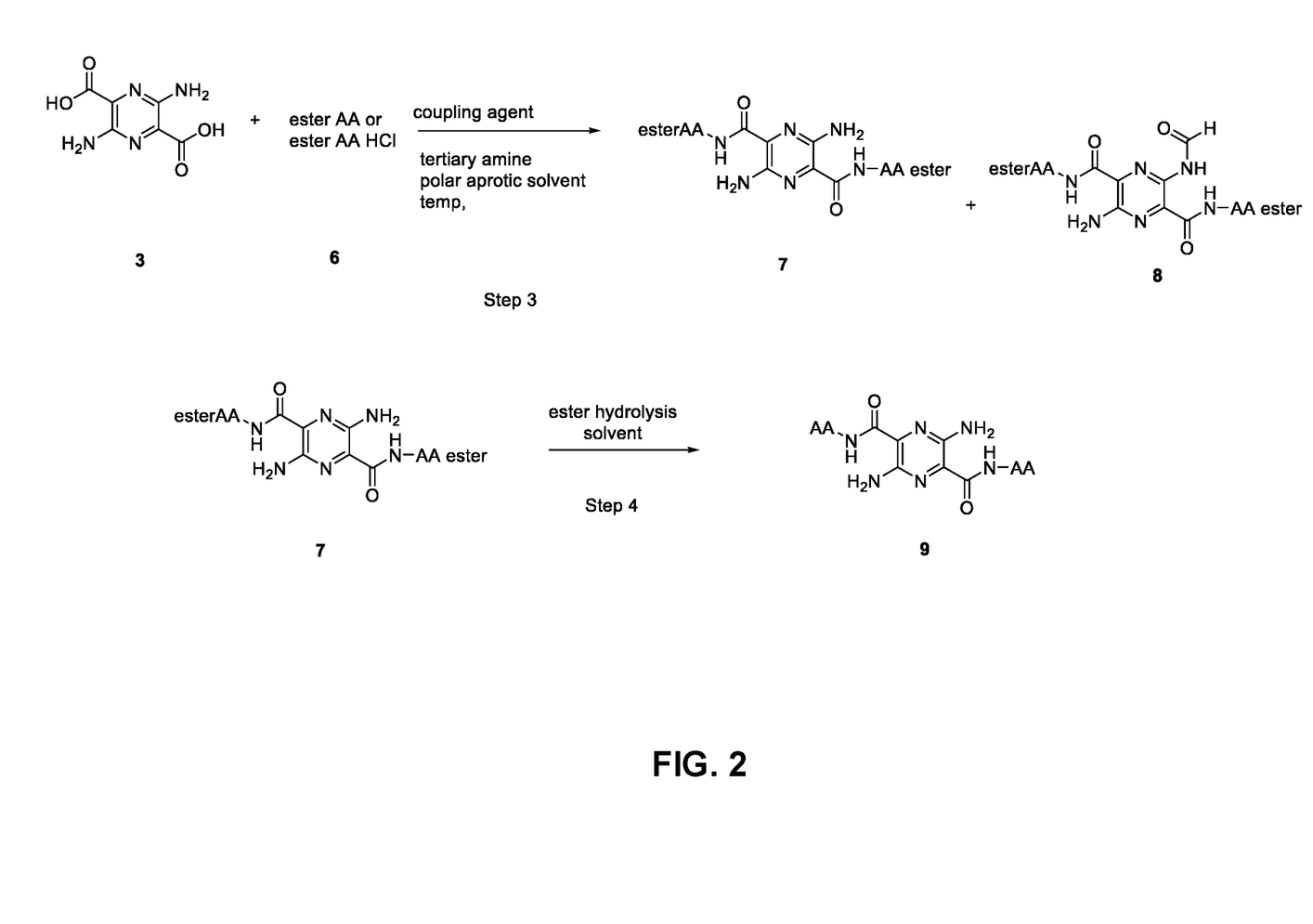
FIG. 2 illustrates reactions and optimization of Step 3 of the process.

Provided herein are methods for preparing the compound of Formula (I) as shown in FIG. 2. Advantageously, it was discovered that a new activation (coupling) agent, ethyl-2-cyano-2-(hydroxyimino)acetate (Oxyma) in Step 3, yields the intermediate compound 7 in comparable yields as other coupling reagents with reduced amounts of the N-formyl impurity, compound 8, that would carry through the process to prepare compound 9. The methods disclosed herein include process improvements such as optimal mole ratios of the starting materials and a method for recovering the key intermediate. The desired compounds comprising the compound of Formula (I) are easily recrystallized, do not require chromatography to remove the N-formyl impurity (compound 8), easily scalable, applicable to GMP, and can be directly used in the Step 4 of the process forming compound 9 as shown in FIG. 2.

(I) Method to Prepare the Compound comprising Formula (I)

The present disclosure encompasses methods for preparing the compound comprising the compound of Formula (I), Formula (I)

the methods comprising contacting 3,6-diamino-2,5-pyrazinedicarboxylic acid, an ester of an amino acid (AA ester) or a salt thereof, a polar aprotic solvent, a tertiary amine, ethyl-2-cyano-2-(hydroxyimino)acetate, and 1-ethyl-3-(3-dimethylaminopropyl) carbodiimide (EDC) hydrochloride under suitable reaction conditions to form the compound of Formula (I); wherein the ester portion of the AA ester is an $C_1$-$C_{10}$ unsubstituted alkyl or a $C_1$-$C_{10}$ substituted alkyl.

(a) 3,6-diamino-2,5-pyrazinedicarboxylic acid 3,6-Diamino-2,5-pyrazinedicarboxylic acid 3 (MB-301) is prepared by the hydrolysis in 98% $H_2SO_4$ of 3,6-diamino-2,5-pyrazinecarbonitrile 1 forming 3,6-diamino-2,5-pyrazinedicarboxamide 2. The base hydrolysis of the bisamide 2 using an excess of aqueous KOH yields 3,6-diamino-2,5-pyrazinedicarboxylic acid 3 as shown in FIG. 1. This material can be isolated in high purity with low amounts of residual water (KF<0.5%).

(b) An Ester of an Amino Acid or Salt Thereof

A variety of the amino acid portion in the ester acid (AA ester) or salt thereof may be used in the method. In various embodiments, the amino acid portion of the AA ester or salt thereof may be a natural amino acid, an unnatural amino acid, or a synthetic amino acid. Non-limiting examples of these amino acids include alanine, arginine, asparagine, aspartate, cysteine, glutamate, glutamine, glycine, histidine, isoleucine, leucine, lysine, methionine, phenylalanine, proline, serine, threonine, tryptophan, tyrosine, and valine. Other amino acids include, by way of non-limiting example, N-acylamino acids, and hydroxy homologue compounds. In one preferred embodiment, the amino acid portion of the ester amino acid is serine.

The amino acid portion of the AA ester or salt thereof may be a (R) configuration, a (S) configuration, an unequal mixture of a (R) and (S) configuration, or a racemic mixture. In one preferred embodiment, the configuration of the amino acid portion of the AA ester or salt thereof is a (R) configuration.

The ester portion of the ester of the amino acid (ester AA) may be an $C_1$-$C_{10}$ unsubstituted alkyl or a $C_1$-$C_{10}$ substituted alkyl. In various embodiments, the ester portion of the ester of the amino acid (ester AA) may be an $C_1$-$C_8$ unsubstituted alkyl or a $C_1$-$C_8$ substituted alkyl. In certain embodiments, the ester portion of the ester amino acid may be methyl, ethyl, tert-butyl, or benzyl. In one preferred embodiment, the ester portion of the ester amino acid is benzyl.

The ester amino acid (AA ester) may be a base or salt thereof. Non-limiting examples of physiologically acceptable salts thereof may be hydrochlorides, hydrosulfates, ammonium salts, potassium salts, calcium salts, magnesium salts and sodium salts of amino acids. In one preferred embodiment, the salt of the AA ester is a hydrochloride salt.

Non-limiting examples of the AA ester or salt thereof may be (S)-alanine methyl ester HCl, (R)-serine benzyl ester HCl, or (S)-proline ethyl ester hydro sulfate. In one preferred embodiment, the AA ester or salt thereof may be (R)-serine benzyl ester HCl.

In general, the AA ester or salt thereof to 3,6-diamino-2,5-pyrazine dicarboxylic acid are presented at a mole ratio of about 2.01:1.0 to about 2.20:1.0. In various embodiments, the mole ratio of the ester amino acid or salt thereof to 3,6-diamino-2,5-pyrazine dicarboxylic acid ranges from about 2.01:1.0 to about 2.20:1.0, from about 2.05:1.0 to about 2.15:1.0, or from about 2.08:1.0 to about 2.12:1.0. In one preferred embodiment, the mole ratio of the ester amino acid or salt thereof to 3,6-diamino-2,5-pyrazine dicarboxylic acid may be about 2.10:1.0.

(c) A Polar Aprotic Solvent

A variety of polar aprotic solvent may be used in the process. With the limited solubility of 3,6-diamino-2,5-pyrazine dicarboxylic acid, the polar aprotic solvent with the other components in the method provide increased solubility and increased reactivity. Non-limiting examples of suitable polar aprotic solvents are N,N-dimethylformamide (DMF), N—N-dimethylacetamide (DMAc), and dimethylsulfoxide (DMSO). In one preferred embodiment, the polar aprotic solvent used in the method is N,N-dimethylformamide.

Generally, polar aprotic solvent to the 3,6-diamino-2,5-pyrazine are present at a volume (mL) to weight (gram) ratio from about 10.0:1.0 to about 100.0:1.0. In various embodiments, the volume to weight ratio of the polar aprotic solvent to the 3,6-diamino-2,5-pyrazine may range from 10.0:1.0 to about 100.0:1.0, from about 12.0:1.0 to about 75.0:1.0, from about 15.0:1.0 to about 50.0:1.0, or from about 18.0:1.0 to about 25.0:1.0. In one preferred embodiment, the volume to weight ratio of the polar aprotic solvent to the 3,6-diamino-2,5-pyrazine may be about 20.0:1.0.

(d) A Tertiary Amine

Numerous tertiary amines may be used in the method. The tertiary amine enhances the solubility of the 3,6-diamino-2,5-pyrazine with the other components in the method. Non-limiting examples of suitable tertiary amines may be trimethylamine, triethylamine, tripropylamine, diisopropylethylamine, tributylamine, 4-methylmorpholine, 4-ethylmorpholine, N-methylpyrrolidine, and N-methylpiperidine. In one preferred embodiment, the tertiary amine used in the method is diisopropylethylamine.

In general, the tertiary amine to 3,6-diamino-2,5-pyrazinedicarboxylic acid are presented at a mole ratio from about 2.01:1.0 to about 2.30:1.0. In various embodiments, the mole ratio of the tertiary amine to 3,6-diamino-2,5-pyrazinedicarboxylic acid may range from about 2.01:1.0 to about 2.30:1.0, from about 2.05:1.0 to about 2.25:1.0, or from about 2.15:1.0 to about 2.25:1.0. In one preferred embodiment, the mole ratio of the tertiary amine to 3,6-diamino-2,5-pyrazinedicarboxylic acid may be about 2.20:1.0.

(e) Coupling Reagent

A combination of two reagents facilitate the coupling of the ester AA or salt thereof to the 3,6-diamino-2,5-pyrazinedicarboxylic acid. These two reagents are 2-cyano-2-(hydroxyimino)acetate (Oxyma) and 1-ethyl-3-(3-dimethylaminopropyl) carbodiimide hydrochloride (EDC HCl).

In general, EDC HCl and the 3,6-diamino-2,5-pyrazinedicarboxylic acid are presented at a mole ratio from about 2.20:1.0 to about 2.50:1.0. In various embodiments, the mole ratio of the EDC HCl to the 3,6-diamino-2,5-pyrazinedicarboxylic acid may range from about 2.20:1.0 to about 2.50:1.0, from about 2.20:1.0 to about 2.40:1.0, or from about 2.25:1.0 to about 2.35:1.0. In one preferred embodiment, the mole ratio of the EDC HCl to the 3,6-diamino-2,5-pyrazinedicarboxylic acid may be about 2.30:1.0.

Generally, 2-cyano-2-(hydroxyimino)acetate (Oxyma) and 3,6-diamino-2,5-pyrazinedicarboxylic acid are presented at a mole ratio from about 2.20:1.0 to about 2.50:1.0. In various embodiments, the mole ratio of 2-cyano-2-(hydroxyimino)acetate (Oxyma) to 3,6-diamino-2,5-pyrazinedicarboxylic acid may range from about 2.20:1.0 to about 2.50:1.0, from about 2.25:1.0 to about 2.45:1.0, from about 2.30:1.0 to about 2.40:1.0. or from about 2.34:1.0 to about 2.38:1.0. In one preferred embodiment, the mole ratio of 2-cyano-2-(hydroxyimino)acetate (Oxyma) to 3,6-diamino-2,5-pyrazinedicarboxylic acid may be 2.36:1.0.

(f) Reaction Conditions

The method comprises adding the above-described reagents to form the compound comprising Formula (I). These reagents can be added in any sequential order, in any combination, or all at once. Once all these regents are contacted, the method commences for the preparation of the compound comprising Formula (I). In one preferred embodiment, the method comprises (a) contacting the 3,6-diamino-2,5-pyrazinedicarboxylic acid with the ester amino acid or salt thereof in a polar aprotic solvent in a vessel to form a suspension; (b) contacting the suspension from step (a) with a tertiary amine; (c) contacting the suspension from step (b) with ethyl-2-cyano-2-(hydroxyimino) acetate; and (d) contacting the suspension from step (c) with 1-ethyl-3-(3-dimethylaminopropyl) carbodiimide HCl (EDC HCl) to form the compound comprising Formula (I).

The method, as described herein, may be conducted in batch mode, semi-continuous mode, or continuous mode.

The method typically is performed under ambient pressure. The method may also be conducted under an inert atmosphere, for example under helium, nitrogen, argon, and a combination thereof.

In general, the method will be conducted at a temperature from about −10° C. to about 30° C. In various embodiments, the temperature of the method may range from about −10° C. to about 30° C., from about −2° C. to about 25° C., or from about −0° C. to about 20° C. In one embodiment, the reaction may be conducted at temperature at −0° C. to about 20° C.

Generally, the method is allowed to proceed for a sufficient period of time until the reaction is complete, as determined by any method known to one skilled in the art, such as HPLC, UPLC, proton nuclear magnetic resonance (e.g., $^1$H NMR), or carbon magnetic resonance (e.g., $^{13}$C NMR). The duration of the method may range from about 1 hour to about 48 hours. In some embodiments, the duration of the method may range from about 1 hour to about 2 hours, from about 2 hours to about 4 hours, from about 4 hours to about 8 hours, from about 8 hours to about 12 hours, from about 12 hours to about 18 hours, from about 18 hours to about 24 hours, from about 24 hours to 36 hours, or from about 36 hours to about 48 hours. In an exemplary embodiment, the method may be allowed to proceed for about 24 hours.

In this context, a "completed method" generally means that the reaction mixture contains a significantly diminished amount of 3,6-diamino-2,5-pyrazinedicarboxylic acid. Typically, the amount of 3,6-diamino-2,5-pyrazinedicarboxylic acid remaining in the reaction mixture at the end of the reaction may be less than about 5%, less than about 2%, or less than about 1%.

After the method is deemed complete, the suspension comprising the compound of Formula (I), trace amounts of 3,6-diamino-2,5-pyrazinedicarboxylic acid, and the ester amino acid is filtered to remove traces of 3,6-diamino-2,5-pyrazinedicarboxylic acid. After the separation of 3,6-diamino-2,5-pyrazinedicarboxylic acid, the compound of Formula (I) is precipitated by adding the filtrate into water. As appreciated by the skilled artisan, an excess of water is required to ensure the compound of Formula (I) is completely precipitated. After the compound is completely precipitated, the compound of Formula (I) is initially washed with additional water and then isolated by means known in the art such as filtration or centrifugation. The water used in the precipitation may be deionized water, distilled water, distilled deionized water, or potable (tap) water.

The compound of Formula (I) may have a yield of at least about 70%. In various embodiments, the compound of Formula (I) may have a yield of at least about 75%, at least about 80%, at least about 85%, at least about 90%, or greater than 90%. In specific embodiments, the yield may be at least about 80%.

In general, the yield of the compound of Formula (I) prepared by the method disclosed herein is comparable to the yield of said compound prepared by prior art methods. Yet, the relative amounts of impurities which can carry through the next method step are reduced significantly.

The compound of Formula (I) may have a purity greater than about 95% as measured by high-performance liquid chromatography (HPLC), ultra-performance liquid chromatography (UPLC), or other methods known in the art. In various embodiments, the compound of Formula (I) may have a purity greater than about 95%, greater than about 97%, or greater than about 98% as measured by HPLC or UPLC. In one preferred embodiment, the compound of Formula (I) has a purity greater than 97% as measured by HPLC.

(g) Exemplary Embodiments

In some embodiments, the polar aprotic solvent is N,N-dimethylformamide; (R)-serine benzyl ester HCl and 3,6-diamino-2,5-pyrazinedicarboxylic acid are present at a mole ratio from about 2.01:1.0 to about 2.20:1.0; EDC HCl to 3,6-diamino-2,5-pyrazinedicarboxylic acid are present at a mole ratio ranging from about 2.20:1.0 to about 2.50:1.0; ethyl-2-cyano-2-(hydroxyimino)acetate and 3,6-diamino-2,5-pyrazinedicarboxylic acid are present at a mole ratio ranging from about 2.20:1.0 to about 2.50:1.0; diisopropylethylamine and 3,6-diamino-2,5-pyrazinedicarboxylic acid are present at a mole ratio ranging from about 2.10:1.0 to about 2.30:1.0; N,N-dimethylformamide and 3,6-diamino-2,5-pyrazinedicarboxylic acid are present at a volume (mL) to weight (gram) ratio from about 10.0:1.0 to about 100.0:1.0; and the contacting of each step occurs at a temperature from about −10° C. to about 30° C. The compound comprising Formula (I) has an isolated yield of at least 70% or at least 80% and a purity greater than 95%.

In certain embodiments, the polar aprotic solvent is N,N-dimethylformamide; (R)-serine benzyl ester HCl and 3,6-diamino-2,5-pyrazinedicarboxylic acid are presented at a mole ratio of about 2.10:1.0; EDC HCl and 3,6-diamino-2,5-pyrazinedicarboxylic acid are present at a mole ratio of about 2.30:1.0; ethyl-2-cyano-2-(hydroxyimino)acetate and 3,6-diamino-2,5-pyrazinedicarboxylic acid are present at a mole ratio of about 2.36:1.0; diisopropylethylamine and 3,6-diamino-2,5-pyrazinedicarboxylic acid are present at a mole ratio of about 2.20:1.0; N,N-dimethylformamide and 3,6-diamino-2,5-pyrazinedicarboxylic acid are present at a volume (mL) to weight (gram) ratio of is about 20.0:1.0; and contacting of each step of the method occurs at the temperature from about 0° C. to about 20° C. The compound comprising Formula (I) has an isolated yield of at least 80% and a purity greater than 97%.

Definitions

When introducing elements of the embodiments described herein, the articles "a", "an", "the" and "said" are intended to mean that there are one or more of the elements. The term "about" is intended to represent ±20%.

In this disclosure, "comprises," "comprising," "containing," and "having" and the like can have the meaning ascribed to them in U.S. Patent Law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. In this specification when using an open ended term, like "comprising" or "including," it is understood that direct support should be afforded also to "consisting essentially of" language as well as "consisting of" language as if stated explicitly and vice versa.

As various changes could be made in the above-described methods without departing from the scope of the invention, it is intended that all matter contained in the above description and in the examples given below, shall be interpreted as illustrative and not in a limiting sense.

EXAMPLES

Example 1: Initial Screening Experiments

A set of screening experiments were conducted to examine other coupling reagents, bases, and polar solvents which would produce a simplified/less complex mixture where dibenzyl 2,2'-(3,6-diaminopyrazine-2,5-dicarbonyl)bis(azanediyl)(2R,2'R)-bis(3-hydroxypropanoate) 3 could be isolated in an improved yield with greater purity and less by-products.

Propanephosphonic acid anhydride (T3P) was chosen as candidate based on the practical aspects of implementing the reagent into a process. T3P-mediated coupling reaction rates are typically very fast and, thus, racemization is usually suppressed. The reagent can be dose controlled to mitigate exothermic behavior and work-up procedures usually involve an aqueous quench and phase separation. T3P is commercially available in several common solvents at a 50% component by mass such as T3P in DMF, MeCN, and EtOAc. Dicyclohexylcarbodiimide (DCC) and N-hydroxysuccinimide (NHS) were also examined as the coupling reagent for the preparation of dibenzyl 2,2'-((3,6-diaminopyrazine-2,5-dicarbonyl)bis(azanediyl)(2R,2'R)-bis(3-hydroxypropanoate) 3.

A series of common organic bases were also screened to determine (a) solubility of ammonium carboxylate of 3,6-diamino-2,5-pyrazinedicarboxylic acid 3 and (b) the influence of pKa (conjugate acid) on reaction conversion. An important aspect of the process is that the solubility of 3,6-diamino-2,5-pyrazinedicarboxylic acid 3 is poor in DMF. However, reaction conversion and solubility is improved by using EDC-activated ester, DIPEA, and eventually the dibenzyl 2,2'-((3,6-diaminopyrazine-2,5-dicarbonyl)bis(azanediyl)(2R,2'R)-bis(3-hydroxypropanoate) 4.

Finally, a solvent screen was performed to identify suitable solvents to be used in the T3P coupling process. Of the organic solvents examined, 3,6-diamino-2,5-pyrazinedicarboxylic acid 3 had the highest solubility (not quantified) in N,N-dimethylformamide (DMF).

Figure 3:
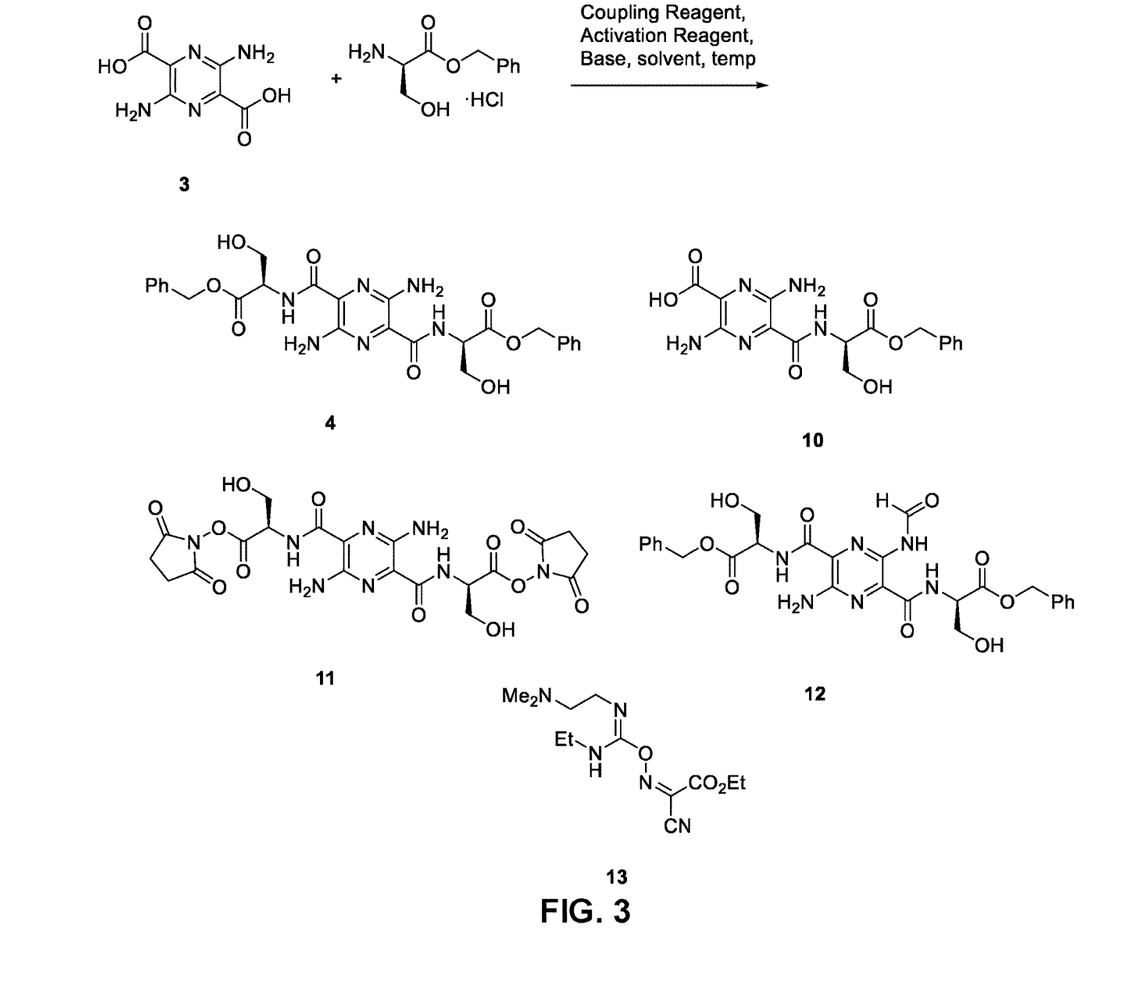
FIG. 3 illustrates the impurities derived during process development.

The general procedure is as follows: Into a vial equipped with a magnetic stirring bar under a nitrogen atmosphere was placed D-serine benzyl ester hydrochloride and the solvent. The solution was cooled in an ice bath and purged with nitrogen. Then, the base was added followed by 3,6-diaminopyrazine-2,5-dicarboxylic acid 3 were added. A red suspension formed and was stirred for 15 minutes. Then, the coupling reagent was added in one portion at 0° C. The suspension was stirred for a period of time and analyzed by HPLC and UPLC. The Table below shows the results of these screening experiments. Each reaction was quenched in water, analyzed by UPLC or HPLC, and the residual amounts and conversion percentage of the 3,6-diaminopyrazine-2,5-dicarboxylic 3 was measured. Impurities found are shown in FIG. 3.

TABLE 1

Screening Experiments

| Trial # | 3,6-diaminopyrazine-2,5-dicarboxylic acid 3 (amount, equiv) | Eq. of D-serine benzyl ester hydrochloride 2 | Coupling Agent (Activation Reagent and Equiv) | Organic base and eq | Solvent (vol) | Temp | % Conversion of 3 (Area under Curve (AUC)) | Comments |
|---|---|---|---|---|---|---|---|---|
| 1 | 100 mg (1.0 eq) | 2.0 eq. | T$_3$P (3.0 eq) | TEA (8.0 eq) | DMF (40) | 0° C. to RT | 52% | |
| 2 | 100 mg (1.0 eq) | 2.0 eq. | T$_3$P (3.0 eq) | NMM (8.0) | DMF (40 vol) | 0° C. to RT | 42.9% | |
| 3 | 100 mg (1.0 eq) | 2.0 eq. | T$_3$P (3.0 eq) | NMI (8.0 eq) | DMF (40 vol) | 0° C. to RT | 51.4% | |
| 4 | 100 mg (1.0 eq) | 2.0 eq. | T$_3$P (3.0 eq) | Pyridine (8.0 eq) | DMF (40v01) | 0° C. to RT | 5.9% | |
| 5 | 200 mg | 2.0 eq. | T$_3$P (3.0 eq) | DIPEA (6.0 eq) | DMF (30 vol) | 0° C. to RT | 72.6% | |

TABLE 1-continued

Screening Experiments

| Trial # | 3,6-diaminopyrazine-2,5-dicarboxylic acid 3 (amount, equiv) | Eq. of D-serine benzyl ester hydrochloride 2 | Coupling Agent (Activation Reagent and Equiv) | Organic base and eq | Solvent (vol) | Temp | % Conversion of 3 (Area under Curve (AUC)) | Comments |
|---|---|---|---|---|---|---|---|---|
| 6 | 200 mg (1.0 eq) | 2.0 eq. | T$_3$P (2.3 eq) | DIPEA | EtOAc | 0° C. to RT | 20.9% | Reaction not a free-flowing slurry |
| 7 | 200 mg (1.0 eq) | 2.0 eq. | T$_3$P (2.3 eq) | DIPEA (9.0 eq) | MeCN (15 vol) | 0° C. to RT | 56.4% | |
| 8 | 1.0 g | 2.0 eq. | T$_3$P (2.3 eq) | DIPEA (5.0 eq) | MeCN (15) | 0° C. to RT | 86.5% | Recovered 56% of 3 and observed monoamide 10. |
| 9 | 200 mg (1.0 eq) | 2.0 eq. | DIC (2.5 eq) | DIPEA (2.5 eq) | MeTHF (15 vol) | 0° C. to RT, then at 50 C | 0% | No conversion at 0° C. or 50° C. |
| 10 | 200 mg | 2.0 eq. | NHS (2.05 eq) and EDC HCl (2.2 eq) | None | DCM (20 vol) | 0° C. to RT | 0% | Recovered NHS ester 11. |

As the results in the above table indicate, the screening experiments showed that other coupling reagents were not as effective as EDC HCl using HOBt as an activating reagent. The monoamide by-product 10, was observed in various cases indicating T3P was not an effective coupling reagent.

Due to the poor solubility of 3,6-diamino-2,5-pyrazinedicarboxylic acid 3, a polar aprotic solvent was needed to increase the solubility, increase the reaction rate, and improve the yield of the process to prepare compound 4. These results show an improved coupling agent was needed to improve the conversion, reduce racemization, and reduce the amounts of by-products.

Example 2: Screening Experiments Using Ethyl Cyanohydroxyiminoacetate (Oxyma)

HOBt was used as an activating agent in order to increase reaction rate of the coupling and, thus, suppress racemization of the D-serine benzyl ester hydrochloride. Anhydrous HOBt has been noted to have thermal hazards associated with its handling/isolation. Although the hydrated form has been used in other processes without incident and the material has reasonably good safety profile, concerns have been raised regarding the isolation of dibenzyl 2,2'-(3,6-diaminopyrazine-2,5-dicarbonyl)bis(azanediyl)(2,R2'R)-bis(3-hydroxypropanoate) 4 and the by-product formation. These concerns warranted investigations for alternative coupling reagents and conditions.

One advantage that the procedures for preparing dibenzyl 2,2'-((3,6-diaminopyrazine-2,5-dicarbonyl)bis(azanediyl) (2R,2'R)-bis(3-hydroxypropanoate) 4 was that is used D-serine benzyl ester hydrochloride, EDC·HCl, HOBt·H$_2$O, DIPEA, and DMF. As compared to the other coupling conditions, described above and in the literature, was that 3,6-diamino-2,5-pyrazinedicarboxylic acid 3 became soluble as the reaction progressed. This increased solubility increased the reaction conversion and suppressed racemization. The combination of EDC, base, possibly dibenzyl 2,2'-((3,6-diaminopyrazine-2,5-dicarbonyl)bis(azanediyl) (2R,2'R)-bis(3-hydroxypropanoate) 4, and additive was hypothesized to increase the solubility of 3,6-diamino-2,5-pyrazinedicarboxylic acid 3 in the process. To this end, Oxyma (ethyl cyanohydroxyiminoacetate), a commercially available activation agent commonly used was screened as a replacement for HOBt.

In order to get a comparison between Oxyma and HOBt, small scale experiments were conducted to determine the yield and the by-products in the isolated dibenzyl 2,2'-(3,6-diaminopyrazine-2,5-dicarbonyl)bis(azanediyl)(2R,2'R)-bis (3-hydroxypropanoate) 4.

The general procedure using Oxyma or HOBt is as follows: Into a round bottom flask equipped with overhead stirring and a nitrogen inlet was placed D-serine benzyl ester hydrochloride and the solvent. The solution was cooled in an ice bath and purged with nitrogen. Then, the base was added followed by 3,6-diaminopyrazine-2,5-dicarboxylic acid 3. A red suspension formed. After stirring for 15 minutes, the coupling reagent and activation reagent was added in one portion at 0° C. The suspension was stirred for a period of time and analyzed by HPLC and UPLC. The Tables below shows the results of these screening experiments. Each reaction was quenched in water, analyzed by UPLC or HPLC, and the residual amounts and conversion percentage of the 3,6-diaminopyrazine-2,5-dicarboxylic 3 was measured. Additionally, the amount and assay of the dibenzyl 2,2'-(3,6-diaminopyrazine-2,5-dicarbonyl)bis(azanediyl) (2R,2'R)-bis(3-hydroxypropanoate) 4 was determined.

TABLE 2

HOBt Activated Coupling of 3 Reaction Conditions

| Trial # | 3, 6-Diaminopyrazine-2,5-dicarboxylic acid 3(amount, 1.0 eq.) | Eq. of D-serine benzyl ester hydrochloride | Coupling and Activation Reagents (eq) | Base (eq) | Solvent (vol) | Temp | % Conversion of 3 |
|---|---|---|---|---|---|---|---|
| 11 | 1.0 g | 2.1 eq. | HOBt xH2O(2.36 eq) and EDC-HCl (2.3 eq) | DIPEA (2.2 eq) | DMF 32 vol) | 0° C. to RT | >95% |
| 12 | 0.5 g | 2.1 eq. | HOBtxH$_2$O(2.36 eq) and EDC-HCl (2.3 eq) | DIPEA (2.2 eq) | CH$_3$CN (32 vol) | 0° C. to RT | 50.9% |

TABLE 3

Results from HOBt Activated Coupling of 3

| Trial # | % Yield of Product | Purity (UPLC) | Comments |
|---|---|---|---|
| 11 | 70% | 98.6% | 1.06% N-formyl impurity 12 |
| 12 | X | X | After 72 h, the reaction did not proceed further. |

TABLE 4

Oxyma Activated Coupling of 3 Reaction Conditions

| Trial # | 3, 6-Diaminopyrazine-2,5-dicarboxylic acid 1 (amount, 1.0 eq.) | Eq. of D-serine benzyl ester hydrochloride 2 | Coupling and Activation Reagents (eq) | Base (eq) | Solvent (vol) | Temp | Time | % Conversion |
|---|---|---|---|---|---|---|---|---|
| 13 | 0.5 g | 2.1 | Oxyma (2.36 eq.)•and EDC•HCl (2.3 equiv) | DIPEA (2.2 eq.) | DMF (32 vol) | 0° C. to RT | 24 | >99% |
| 14 | 5.0 g | 2.1 | Oxyma (2.36 eq.)•and EDC•HCl (2.3 equiv) | DIPEA (2.2 eq.) | DMF (32 vol) | 0° C. to RT | 24 | >99% |
| 15 | 1.0 | 2.1 | Oxyma (2.36 eq.)•and EDC•HCl (2.3 equiv) | DIPEA (2.2 eq.) | DMF (20 vol) | 0° C. to RT | 24 h | >99% |
| 16 | 1.0 | 2.1 | Oxyma (2.36 eq.)•and EDC•HCl (2.3 equiv) | DIPEA (2.2 eq.) | DMF (15 vol) and EtOH (10 vol) | 0° C. to RT | 24 h | >99% |
| 17 | 1.0 | 2.1 | Oxyma (2.36 eq.)•and EDC•HCl (2.3 equiv) | DIPEA (2.2 eq.) | DMF (15 vol) and i-PrOH (10 vol) | 0° C. to RT | 24 h | 69.0% |
| 18 | 20.0 g | 2.1 | Oxyma (2.36 eq.)•and EDC•HCl (2.3 equiv) | DIPEA (2.2 eq.) | DMF (20 vol) | 0° C. to RT | 24 h | >99% |
| 19 | 30.0 g | 2.1 | Oxyma (2.36 eq.)•and EDC•HCl (2.3 equiv) | DIPEA (2.2 eq.) | DMF (20 vol) | 0° C. to RT | 24 h | 92% |

TABLE 4-continued

Oxyma Activated Coupling of 3 Reaction Conditions

| Trial # | 3,6-Diaminopyrazine-2,5-dicarboxylic acid 1 (amount, 1.0 eq.) | Eq. of D-serine benzyl ester hydrochloride 2 | Coupling and Activation Reagents (eq) | Base (eq) | Solvent (vol) | Temp | Time | % Conversion |
|---|---|---|---|---|---|---|---|---|
| 20 | 8.0 g | 2.1 | Oxyma (2.36 eq.)•and EDC•HCl (2.3 equiv) | DIPEA (2.2 eq.) | DMF (20 vol) | 0° C. to RT | 24 h | 76% |

TABLE 5

Results from Oxyma Activated Coupling of 3

| Trial # | % Yield of 3 | Purity of 3 (UPLC) | Comments |
|---|---|---|---|
| 13 | 68 | 94.6% | Product contains 2.9-4.2 area % Oxyma, no N-formyl impurity 12 detected. |
| 14 | 74% | 98.32% | Oxyma and N-formyl impurity 12 not detected |
| 15 | 56% | 98.5% and 95.45% | Two crops of product |
| 16 | 61% | 94.84% | Mono product observed in |
| 17 | X | 69.08% | Not worked up. In process sample contained mono amide product 10 and was not free flowing. |
| 18 | 70% | 97.28% | Similar to previous experiments. |
| 19 | 61% | 97.64% | In process sample contained 5% mono amide product 10 and 8% unreacted SM 3. |
| 20 | 28% yield | 98.61% | 0.89% impurity 13 |

As the results show in Tables 2 and 3, the use of HOBt as an activation agent provides good to excellent conversion to form dibenzyl 2,2'-(3,6-diaminopyrazine-2,5-dicarbonyl)bis(azanediyl)(2R,2'R)-bis(3-hydroxypropanoate) 4. Yet, besides the safety issues associate with HOBt, an N-formyl impurity 12 is formed. This N-formyl impurity 12 co-crystallizes with the product and would be difficult to remove from the product. In the past, chromatography was used to separate the N-formyl impurity 12 from the product.

In contrast, as shown in Tables 4 and 5, the use of Oxyma as an activation reagent provides good to excellent conversions. In addition, the N-formyl impurity 12 is not formed. Therefore, crystallization conditions could be developed to produce the dibenzyl 2,2'-((3,6-diaminopyrazine-2,5-dicarbonyl)bis(azanediyl)(2R,2'R)-bis(3-hydroxypropanoate) 4 that does not contain the N-formyl impurity 12. A new unknown impurity in Table 5, Trial 20 was identified and characterized as an Oxyma-EDC impurity 13.

Example 3: Preparation of Dibenzyl 2,2'-((3,6-diaminopyrazine-2,5-dicarbonyl)bis(azanediyl)(2R,2'R)-bis(3-hydroxypropanoate) 4

Into a 1 L jacketed reactor equipped with overhead stirring and a $N_2$ inlet was charged 3,6-diamino-2,5-pyrazinedicarboxylic acid 3 (20.0 g, 10.0 mmoles), D-serine benzyl ester HCl 2 (49.11 g, 212.0 mmol, 2.10 eq), and anhydrous DMF (400 mL, 20 vol). Stirring was initiated and a red colored slurry formed. The reactor was cooled to (0° C. jacket temp; 6° C. internal temp) and diisopropylethylamine (DIPEA, 38.7 mL, 222.1 mmol, 2.2 eq.) was added over a 5 minute period. Upon addition of the DIPEA, the color of the slurry changed from red to orange and no exotherm was detected. To the orange slurry was added ethyl-2-cyano-2-(hydroxyimino)acetate (Oxyma, 33.85 g, 238.2 mmol, 2.36 eq) over 2 minutes. After the addition of the Oxyma, the reaction exothermed from 2° C. to 6° C. and quickly subsided returning to an internal temperature of 2° C. To this mixture was added N-(3-dimethylaminopropyl)-N'-ethylcarbodiimide hydrochloride (EDC HCl, 44.5 g, 232.2 mmol, 2.3 equiv) over 4 minutes. No exotherm was detected and the slurry became very thick. The agitation rate increased from 370 RPM to 500 RPM. The mixture was warmed to 10° C. and then to 20° C. The reaction was stirred at 20° C. for 20 h monitored by ultra-performance liquid chromatography (UPLC). At that time, the mixture contained approximately 1.76 area % of monoamide 10 and <1.0 area % of 3,6-diamino-2,5-pyrazinedicarboxylic acid 3. At that time, the mixture was filtered cold. The filtrate was cooled to (0° C. jacket temp; 2° C. internal temp) and distilled water (500 mL, 25 vol) was slowly added over 45 minutes. The product 3 started precipitating after 370 mL of water (18.5 vol) was added. After the addition of water was complete, the mixture was stirred for 1.5 h at 0° C. and then the mixture was filtered cold producing a filter cake. The jacketed reactor vessel was rinsed with distilled water (2×100 mL), poured over the filter cake, and the filter cake was dried under vacuum (40° C.). The product 4 (42.95 g, 77.7 mmol, 77% yield, 97.28 area %) was obtained as a free flowing solid.

What is claimed is:

1. A method for preparing a compound of Formula (I):

Formula (I)

the method comprising contacting 3,6-diamino-2,5-pyrazinedicarboxylic acid, an ester amino acid ("AA ester") or a salt thereof, a polar aprotic solvent, a tertiary amine, ethyl-2-cyano-2-(hydroxyimino)acetate, and 1-ethyl-3-(3-dimethylaminopropyl)carbodiimide (EDC) hydrochloride under suitable reaction conditions to form the compound of Formula (I);

wherein the ester portion of the AA ester is an $C_1$-$C_{10}$ unsubstituted alkyl or a $C_1$-$C_{10}$ substituted alkyl.

2. The method of claim 1, wherein 3,6-diamino-2,5-pyrazinedicarboxylic acid, the AA ester or salt thereof, the polar aprotic solvent, the tertiary amine, ethyl-2-cyano-2-(hydroxyimino)acetate, and 1-ethyl-3-(3-dimethylaminopropyl)carbodiimide (EDC) hydrochloride are added in any sequential order, in any combination, or added all at once.

3. The method of claim 1, wherein the method comprises:
  (a) contacting 3,6-diamino-2,5-pyrazinedicarboxylic acid with the AA ester or salt thereof in a polar aprotic solvent in a vessel to form a suspension;
  (b) contacting the suspension from step (a) with the tertiary amine;
  (c) contacting the suspension from step (b) with ethyl-2-cyano-2-(hydroxyimino)acetate;
  (d) contacting the suspension from step (c) with 1-ethyl-3-(3-dimethylaminopropyl)carbodiimide (EDC) hydrochloride to form the compound of Formula (I).

4. The method of claim 1, wherein the amino acid portion of the AA ester or salt thereof is a natural amino acid, an unnatural amino acid, or a synthetic amino acid.

5. The method of claim 1, wherein the amino acid portion of the AA ester or salt thereof is a (R) configuration, a(S) configuration, or a racemic mixture.

6. The method of claim 1, wherein the amino acid of the AA ester or salt thereof is (R)-serine.

7. The method of claim 1, wherein the ester portion of the AA ester is a $C_1$-$C_8$ unsubstituted alkyl or a $C_1$-$C_8$ substituted alkyl.

8. The method of claim 1, wherein the ester portion of the AA ester or salt thereof is methyl, ethyl, tert-butyl, or benzyl.

9. The method of claim 1, wherein the ester of the AA ester or salt thereof is (R)-serine benzyl ester or (R)-serine benzyl ester HCl.

10. The method of claim 1, wherein the tertiary amine is selected from the group consisting of trimethylamine, triethylamine, diisopropylethylamine, tripropylamine, tributylamine, 4-methylmorpholine, 4-ethylmorpholine, N-methylpyrrolidine, and N-methylpiperidine.

11. The method of claim 1, wherein the AA ester and 3,6-diamino-2,5-pyrazinedicarboxylic acid are presented at mole ratio from about 2.01:1.0 to about 2.20:1.0.

12. The method of claim 1, wherein EDC HCl and 3,6-diamino-2,5-pyrazinedicarboxylic acid are presented at a mole ratio from about 2.20:1.0 to about 2.50:1.0.

13. The method of claim 1, wherein the ethyl-2-cyano-2-(hydroxyimino)acetate and 3,6-diamino-2,5-pyrazinedicarboxylic acid are presented at a mole ratio from about 2.20:1.0 to about 2.50:1.0.

14. The method of claim 1, wherein the tertiary amine and 3,6-diamino-2,5-pyrazinedicarboxylic acid are presented at a mole ratio from about 2.10:1.0 to about 3.0:1.0.

15. The method of claim 1, wherein the polar aprotic solvent is N,N-dimethylformamide, N—N-dimethylacetamide, or dimethylsulfoxide.

16. The method of claim 1, wherein the polar aprotic solvent and 3,6-diamino-2,5-pyrazinedicarboxylic acid are presented at a volume (mL) to weight (gram) ratio from 10.0:1.0 to about 100.0:1.0.

17. The method of claim 1, wherein the contacting of each step occurs at a temperature ranging from about-10° C. to about 30° C.

18. The method of claim 1, wherein the contacting of each step of the method is conducted under helium, nitrogen, argon, or a combination thereof.

19. The method of claim 1, wherein the compound of Formula (I) has a percent yield of at least 70%.

20. The method of claim 1, wherein the compound of Formula (I) has a purity greater than about 95%.

21. The method of claim 1, wherein the polar aprotic solvent is N,N-dimethylformamide; (R)-serine benzyl ester HCl and 3,6-diamino-2,5-pyrazinedicarboxylic acid are presented at a mole ratio from about 2.01:1.0 to about 2.20:1.0; EDC HCl and 3,6-diamino-2,5-pyrazinedicarboxylic acid are presented at a mole ratio ranging from about 2.20:1.0 to about 2.50:1.0; ethyl-2-cyano-2-(hydroxyimino)acetate and 3,6-diamino-2,5-pyrazinedicarboxylic acid are presented at a mole ratio ranging from about 2.20:1.0 to about 2.50:1.0; diisopropylethylamine and 3,6-diamino-2,5-pyrazinedicarboxylic acid are presented at a mole ratio ranging from about 2.10:1.0 to about 2.30:1.0; N, N-dimethylformamide and 3,6-diamino-2,5-pyrazinedicarboxylic acid are presented at a volume (mL) to weight (gram) ratio from 10.0:1.0 to about 100.0:1.0; and the contacting of each step occurs at a temperature from about −10° C. to about 30° C.

22. The method of claim 21, wherein the compound of Formula (I) has a percent yield of at least 70%.

23. The method of claim 21, wherein the compound of Formula (I) has a purity greater than about 95%.

24. The method of claim 1, wherein the polar aprotic solvent is N,N-dimethylformamide; (R)-serine benzyl ester HCl and 3,6-diamino-2,5-pyrazinedicarboxylic acid are presented at a mole ratio of about 2.10:1.0; EDC HCl and 3,6-diamino-2,5-pyrazinedicarboxylic acid are presented at a mole ratio of about 2.30:1.0; ethyl-2-cyano-2-(hydroxyimino)acetate and 3,6-diamino-2,5-pyrazinedicarboxylic acid are presented at a mole ratio of about 2.36:1.0; diisopropylethylamine and 3,6-diamino-2,5-pyrazinedicarboxylic acid are presented at a mole ratio of about 2.20:1.0; N,N-dimethylformamide and 3,6-diamino-2,5-pyrazinedicarboxylic acid are presented at a volume (mL) to weight (gram) ratio of is about 20.0:1.0; and contacting of each step of the method occurs at the temperature from about 0° C. to about 20° C.

25. The method of claim 24, wherein the compound of Formula (I) has a percent yield of at least 80%.

26. The method of claim 24, wherein the compound of Formula (I) has a purity greater than about 98%.

* * * * *